United States Patent [19]

Katsoulis et al.

[11] Patent Number: 5,296,623

[45] Date of Patent: Mar. 22, 1994

[54] DIRECT PROCESS FOR THE PREPARATION OF ACTIVATED ANTIPERSPIRANT SALTS

[75] Inventors: Dimitris E. Katsoulis, Midland, Mich.; Walter J. Carmody, Port Jervis, N.Y.

[73] Assignee: Somerville Technology Group, Inc., Huguenot, N.Y.

[21] Appl. No.: 765,796

[22] Filed: Sep. 26, 1991

Related U.S. Application Data

[62] Division of Ser. No. 484,288, Feb. 26, 1990, abandoned.

[51] Int. Cl.$^5$ ............................ C07F 7/00; C07F 5/06
[52] U.S. Cl. ...................................... 556/27; 556/28; 556/55; 556/56; 424/66; 424/68
[58] Field of Search ....................... 556/27, 28, 55, 56; 424/66, 68

[56] References Cited

U.S. PATENT DOCUMENTS

| | | | |
|---|---|---|---|
| 4,148,812 | 4/1979 | Rubino et al. | 260/429.3 |
| 4,331,609 | 5/1982 | Orr | 260/448 R |
| 5,156,834 | 10/1992 | Beckmeyer et al. | 424/47 |
| 5,179,220 | 1/1993 | Katsoulis et al. | 557/27 |
| 5,225,187 | 7/1993 | Carmody | 424/66 |

Primary Examiner—Jose G. Dees
Assistant Examiner—Porfurio Nazario-Gonzalez
Attorney, Agent, or Firm—Kenneth P. Glynn

[57] ABSTRACT

A method of producing activated metal salts useful in antiperspirant compositions is disclosed. The method produces the salt through an acid base reaction wherein an acid is reacted with a metal in basic form. Preferred metals include aluminum and zirconium. Activate aluminum-zirconium hydrohalide and activated aluminum-zirconium-amino acid salts can also be produced by the method of this invention.

6 Claims, No Drawings

DIRECT PROCESS FOR THE PREPARATION OF ACTIVATED ANTIPERSPIRANT SALTS

This is a divisional of copending application Ser. No. 07/484,288 filed on Feb. 26, 1990, now abandoned.

This invention pertains to a direct process for the preparation of activated antiperspirant salts. The process of this invention uses an acid-base neutralization reaction to directly prepare the activated salts without the use of heat or long reaction periods. The neutralization reaction of this invention has a highly desirable result in that the antiperspirant salt formed directly in the process is an activated salt typically having an exceptionally high amount of $Al_{13}$ material.

BACKGROUND OF THE INVENTION

Antiperspirant salts are well known in the personal care industry. Examples of such salts include the halogen, nitrate and sulfate salts of base metals, such as aluminum and zirconium. Well known and widely used antiperspirant salts include aluminum chlorohydrate, and mixtures of aluminum and zirconium chlorohydrate, in both inactivated and activated forms. Lesser known varieties of antiperspirant salts include zirconium chlorohydrate, aluminum and zirconium bromohydrates, iodohydrates, fluorohydrates, nitrohydrates, sulfohydrates and mixtures thereof, in both inactivated and activated forms.

For years, these materials have been prepared according to a process referred to herein as the "standard" antiperspirant salt preparation process. In the standard process, the base metal, such as aluminum, is first oxidized and then hydrolyzed with an acid, such as HCl, in order to make a solution of aluminum chlorohydrate. This process typically takes five or more days to complete depending on the surface area of the aluminum and the concentration. Although the materials obtained according to the standard process provide a measure of protection against perspiration, more recent research in the personal care industry has been directed at improving the materials for use as antiperspirant salts.

Recent research has made it known in the art that antiperspirants salts are polymeric in nature. The ability for the salts to polymerize in water is due to the base metal components (aluminum and zirconium) being polyvalent. In general polyvalent elements, in particular, aluminum and zirconium which have rich hydrolysis chemistry, are capable of forming compounds having a polymeric structure in water. In fact, compounds of aluminum and zirconium in water normally exist in a polymeric state, except when exposed to highly acidic environments.

In a typical sample of an antiperspirant salt composition, a mixture of salt species will be found, with the species being based on the various polymeric states in which the salt exists. Differences in the size, molecular weight and molecular structure of the polymers readily enable one to distinguish the various antiperspirant polymer species. The molecular size, weight and structure of the various species and the relative amounts of the various species present in the antiperspirant salt composition are dependent on the methods and conditions used in processing the antiperspirant salt. It has been found that the concentration of raw materials, pH and temperature of the processing system may all impact the types and relative proportions of the various species formed by the process.

Certain antiperspirant salt species are more useful and desirable than others in the antiperspirant salt compositions. It is recognized in the industry that when these species are present in the antiperspirant salt composition in sufficient quantities, the antiperspirant salt composition is referred to as an "activated antiperspirant salt", "enhanced antiperspirant salt", "super antiperspirant salt", or as preferred by the inventors, an "activated salt". The preferred species has been theorized as having the structure $\{AlO_4Al_{12}(OH)_{24}(H_2O)_{12}\}^{+7}$ and is sometimes referred to as $Al_{13}$, Band III or a "peak 3" material. The "peak 3" terminology come from the fact that it is typically the 3rd peak or 3rd material to be eluted when using High Performance Liquid Chromotography, HPLC, to characterized aluminum chlorohydrate salts (according to the method taught in EP Patent No. 0,256,831). Inactivated salts are typically those that have more of "peak 2" material (theorized as being solublized $Al(OH)_3$ entities held together by H bonding and adjunct Cl ions) than "peak 3" material.

Experimentation has lead to the discovery that antiperspirant salt processing techniques can be practiced which favor the formation of the highly useful species, in particular $Al_{13}$. The resulting activated salts containing these useful and desired species are generally recognized as having a high commercial value.

U.S. Pat. No. 4,359,456 to Gosling et al. describes a process for making an aluminum chlorohydrate salt having a high concentration of the useful species. The process taught by Gosling et al. comprises heating an aqueous solution of $Al_2(OH)_{6-a}X_a$, wherein X represents a halide selected from Cl, Br and I, and a ranges from 0.3 to 4, at a temperature of from 50° to 140° C. for a period of time ranging from one half hour to thirty days. The resulting salt solution is allowed to cool to room temperature and is then spray dried to obtain an activated antiperspirant salt powder.

Several techniques are known in the art and regarded as industry standards for determining whether basic requirements for classifying materials as activated salts have been met. One highly regarded method, referred to generally herein as the "Inward Size Exclusion Chromatography Test", (or "Inward SEC") is disclosed in detail in European Patent Application 0,256,831, which is incorporated herein by reference. In the calculations for determining activation of the salts, according to the Inward SEC method, the area of chromatography peak 3 is compared to that of the total area of all peaks eluted by the sample. A test used by the present inventor generally utilizes the methods, equipment and techniques of the Inward SEC test, but compares the area of chromatography peak 3 to that of peak 2. This version of the Inward SEC test is known as the "p3:p2 SEC" test. Typical activated salts that are commercially available today have a ratio of the area of peak 3 to peak 2 ranging from 0.2 to 1.2.

Other testing methods include the NMR spectral analysis of $^{27}Al$, as described in "Multinuclear Magnetic Resonance Studies of the Hydrolysis of Aluminum (III). Part 8. Base Hydrolysis monitored at Very High Magnetic Field" J. W. Akitt and J. M. Elders, J. Chem. Soc., Dalton Trans. 1988, 1347- 1355, wherein activated salts exhibit an intense resonance at 63.1 ppm. Yet another test for determining activation involves determining the conductivity of solutions of antiperspirant salt materials. Conductivity increases with increased activation of the salt material. Typically a conductivity value over 3.0 mmhos$^{-1}$/cm represents an activated salt.

In general, a salt classified as being an activated salt according to only one of the above tests will also meet the requirements to be classified as activated by the other tests. Overall, an activated salt is one having higher efficacy when used in antiperspirant formulations.

It is an object of this invention to provide a process for the preparation of novel activated antiperspirant salts using a standard acid-base neutralization reaction.

It is further an object of this invention wherein the process comprises the reaction between a hydroxide of a base metal and a strong acid to produce the activated antiperspirant salt.

It is further an object of this invention wherein the process comprises the reaction between a hydroxide of a base metal, a strong acid and $ZrO(OH)X$ or $ZrOX_2$, where X is selected from Cl, Br and I, to produce an activated aluminum- zirconium salts.

It is further an object of this invention wherein the process comprises a method for making activated aluminum- zirconium-amino acid salts.

THE INVENTION

This invention relates to a direct process for the formation of novel activated antiperspirant salts. The process of the invention does not require applying heat to the reactants or the reaction products in order to achieve an activated salt. The novel activated salts can be produced by the process of this invention at room temperature or even below. However, heating of the reactants or reaction products may be optionally carried out to modify the chromatographic profile of the products, particularly if it is desired to shift some of the materials eluted at the peak 1 position to the peak 3 position.

One form of activated salts, herein referred to as standard activated salts, may be produced by the acid-base neutralization reaction between a hydroxide or carbonate of a base metal, such as aluminum or zirconium; and an acid, such as HCl, HBr, HI, HF, $HNO_3$, $AlX_3$, $ZrX_4$, $ZrOX_2$ and $ZrO(OH)X$; where X is selected from Cl, Br and I. The strong acid and the strong base react stoichiometrically and completely to form a salt of the acid and base. In the case of the hydrogen containing (Arrhenius-type) acids water is also formed as a by-product of the neutralization reaction. A standard activated salt produced by the method of this invention can be represented, for example, by $Al_2(OH)_5Cl \cdot nH_2O$ where n has the value of 1 or greater. The activated salt are actually a distribution of various Al derivatives which are abbreviated by the formula above.

Another form of activated salts, herein referred to as activated aluminum-zirconium hydrohalide salts or A-Z-H salts, are produced by the reaction between an aluminum hydroxide; one or more acids, such as HCl, HBr, HI, HF, $HNO_3$, $AlX_3$, and $ZrX_4$; and an amount of a zirconium acid selected from zirconyl hydroxy halide, $ZrO(OH)X$ and zirconyl oxo halide, $ZrOX_2$; where X is as described above. The resulting aluminum-zirconium hydrohalide salt can be represented, for example, by $Al_4Zr(OH)_{12}Cl_4 \cdot nH_2O$, where n is as described above. The aluminum-zirconium hydrohalide salts are a distribution of Al and Zr derivatives abbreviated by the formula above.

Another form of activated salts, herein referred to as activated aluminum-zirconium-amino acid salts or activated AZG salts, are produced by the co-acidification of an aluminum hydroxide and a basic zirconium carbonate followed by the addition of an amino acid such as glycine. Alternatively the activated AZG salts can be formed by the individually acidifying the aluminum hydroxide and the basic zirconium carbonate, adding an amino acid such as glycine to one of the resulting activated salt solutions and combining the two solutions.

The process for preparing the standard activated salts comprises reacting the hydroxide or carbonate of a base metal, the base metal being selected from the group consisting of aluminum, zirconium and mixtures thereof, with an acid selected from the group consisting of HCl, HBr, HI, HF, $HNO_3$, $AlX_3$, $ZrX_4$, $ZrO(OH)X$, $ZrOX_2$ and mixtures thereof, where X is selected from Cl, Br and I to thereby form a standard activated salt. The reaction conditions for the preparation of the standard activated salts of this invention are rather broad.

The materials used in the reaction are known in the art and commercially available or can be produced from known methods. Several forms of the base metals are commercially available. For example, aluminum hydroxide sold under the names Aluminum Hydroxide Wet Gel, WG-100 and Aluminum Hydroxide Dried Gel U.S.P. can be purchased from Chattem Chemicals. Aluminum hydroxide can also be produced by the reaction between $NaAlO_2$ and $CO_2$ or the reaction between $AlCl_3 \cdot 6H_2O$ and $M_2CO_3 \cdot 1^1/_3H_2O$, where M is selected from K, Na, $NH_4$ and others. The starting materials for these reactions are readily available. Zirconium Carbonate, another useful base metal, can be purchased as a paste from Magnesium Electron.

The acids used in the method of the instant invention are commercially available in various concentrations or can be produced using methods known in the art. For example $AlCl_3$ can be produced from the reaction between Al metal and HCl and $ZrO(OH)Cl$ can be produced from the reaction between $3ZrO_2CO_2 \cdot H_2O$ and HCl. Acids, such as HCl, HBr, HF, $HNO_3$, $AlCl_3$, $ZrCl_4$, $ZrO(OH)Cl$ and $ZrOCl_2$, are useful in any available concentration.

Any amount of acid added to the base metal or base metal added to acid will result in the formation of at least some amount of the standard activated salt thereby the ratio of acid to base used in the process of this invention is not restricted. The amount of the standard activated salt being formed will be stoichiometrically limited by the reactant added in lesser amount. However, from the practical standpoint of employing the process for the preparation of the salts for use antiperspirant applications, the stoichiometric ratio of base to acid is maintained so as to allow complete or nearly complete consumption of both the acid and base. A reaction system in which the amount of acid and base reactants is maintained such that complete or nearly complete neutralization occurs will have a pH of around 4.

There are instances when the excess of an acid may cause desirable or undesirable effects in the antiperspirant composition. For instance, when the reaction system contains an excess of acid the antiperspirant formulated from the standard activated salt may cause irritation to the skin of the user of the antiperspirant. However, when the standard activated salt is intended to be soluble in an alcohol for application in roll-on or spray type antiperspirants, an excess of acid is required. Generally, acidic conditions are needed for antiperspirant salts to be soluble in an alcohol such as ethanol. An undesired acidic solution can generally be neutralized by the addition of a strong base such as sodium hydroxide or ammonia.

The amount of base added to the system is not absolutely critical to the invention. However, it will be noted by those skilled in the art that gelling of solutions can occur when high levels of hydroxy base metals are present. The gelling phenomenon can be overcome by diluting the reaction system with a diluent such as water.

In the preparation of standard activated salts, the amount of acid, selected from the group consisting of HCl, HBr, HI, HF, $HNO_3$, $AlX_3$, $ZrX_4$, $ZrO(OH)X$, $ZrOX_2$ and mixtures thereof, where X is as described above, that is to be reacted with the base metal using the process of this invention ranges from greater than 0% by weight to less than 100% by weight of the total weight of all the reactants. The amount of base, comprising the hydroxide or carbonate of a base metal selected from the group consisting of aluminum, zirconium and mixtures thereof, comprises the remaining weight percent of the reaction mixture. It is preferred that the amount of acid and base reacted by the process of the invention are such that the pH of the system after the neutralization reaction is around 4.

The temperature at which the process of the invention is carried out is limited only by the freezing and boiling points of the reactants or the reaction solution. Because most of the reacting materials used in the process of this invention are diluted with or contain water, it is preferred to carry out the process of this invention at temperatures ranging from around 0° C. to around 100° C. The actual freezing and boiling points of the reaction solution may be outside the limits set by the presence of water and therefore may allow operation outside of the preferred range. The actual freezing and boiling points of the reaction solution can typically be calculated or readily determined by direct measurement. Variations in operating pressure may also allow for the reaction to be carried out at temperatures other than those within the preferred range.

It is believed that the presence of heat during the reaction may cause higher amounts of the $Al_{13}$ to be formed thereby resulting in a higher degree of activation. However, When the heat is combined with longer reaction times, this amount of $Al_{13}$ or the degree of activation may decrease. For example, a solution heated at 70° C. for 0.5 hours may have a higher degree of activation than a solution heated at 60° C. for 0.5 hours. Additionally, a solution heated at 60° C. for 0.5 hours may have a higher degree of activation than a solution heated at 70° for 4 hours. It is preferred to keep the residence time relatively short for the reaction. Typically, reaction times of less than 6 hours are sufficient to produce a standard activated salt. Preferably, reaction times of less than 1.5 hours have been found suitable to produce a standard activated salt. Those skilled in the art will know that an acid-base reaction of this type is almost instantaneous and will not require long reaction periods.

Because the reactants are usually found in the form of an aqueous solution the process may be carried out without any further dilution of the reactants. However, if dilution of the reactants is desired, water is the preferred dilution medium. In some instances, dilution may be desired as a means of dissipating heat energy generated by an exothermic acid-base neutralization reaction. In other instances, such as when high levels of base are present in the reaction solution, it may be desirable to dilute the solution to prevent gellation.

As with any acid-base neutralization reaction, the amount of dilution is not critical to the reaction, but should be considered in terms of the economics of the process. It will be obvious to those of ordinary skill in the art that reactants which are more dilute require larger reaction volumes in order to produce the same amount of salt as produced in a system with more concentrated reactants.

The total concentration of the reactants in water is not limited at the low concentration end by any physical or chemical limitations. This reaction will occur satisfactorily when the concentration of the reactants is greater than 0% by weight, based on the weight of the total reactant solution. However, it will be obvious to those skilled in the art that processing will be more expensive when the activated antiperspirant salts are produced with the reactants at a very low concentration in the reaction solution. For practical purposes, the acid and the base reactants together should be comprised at levels at least of 1% by weight based on the weight of the total reaction solution.

The high end of the total concentration of reactants is limited largely by the fact that at when the reactants are highly concentrated in the total solution, the standard activated salt formed by the process of this invention tends to gel. Therefore, together, the acid and base reactants should comprises no more than 50% by weight of the total reaction system. Preferably, water should comprise the rest of the reaction system.

Although there are some limitations based on the concentration of the sum of reactants in the reaction process it is still possible to use highly concentrated reactants. One way this can be achieved is by adding the highly concentrated reactants into a reaction system that contains additional water such that the concentrated reactants are diluted to within the limited concentration ranges after addition into the reaction system. Another way this can be achieved is by using one highly concentrated reactant and one diluted reactant such that when combined they do not exceed the upper limit for the concentration of the combined reactant system.

Upon completion of the reaction the salts can be recovered from the solution by methods known in the art. Examples of these methods include spray drying or a method of quick precipitation such as by the addition of an organic solvent to the system. It is preferred to remove the salts from the solution immediately or very shortly after the completion of the reaction. It is believed that allowing the salts to remain in solution after the reaction has been completed will over a period of time result in a decrease in the degree of activation of the salts.

The degree of activation of the resulting salts may be further increased by using conventional methods known in the art such as heating the salt at high temperatures for a period of time. It is not necessary to additionally use the conventional method for making activated salts as all salts produced by the method of this invention will have some degree of activation. However, it may prove beneficial in some instances in producing a highly activated salt. Typically the use of conventional methods for producing highly activated salts from the activated salts produced by the method of this invention is desired when there is a large degree of "peak 1" material, as determined by HPLC, in the salt composition.

The standard activated salts of this invention can be used in the preparation of antiperspirants compositions, such as sticks, sprays and roll-ons, using known formulations and known methods.

The process of this invention is also useful for producing activated aluminum-zirconium hydrohalide salts (A-Z-H salts). These salts are produced by the reaction between an aluminum hydroxide; one or more acids, such as HCl, HBr HI HF $HNO_3$, $AlX_3$, and $ZrX_4$; and an amount of a zirconium acid selected from zirconyl hydroxy halide, $ZrO(OH)X$ and zirconyl oxo halide, $ZrOX_2$, where X is selected from Cl, Br and I.

The process for preparing the A-Z-H salt has essentially the same operating parameters as for the preparation of standard activated salts except for the addition of $ZrO(OH)X$ or $ZrOX_2$ as a reactant. The $ZrO(OH)X$ or $ZrOX_2$ acts as an acid when added into the reaction medium. Therefore the reaction requires less of the desired acid to ensure complete neutralization of the $Al(OH)_3$. The $ZrO(OH)X$ or $ZrOX_2$ may be added at any step in the reaction process. The preferred method is to blend the zirconyl hydroxy halide or zirconyl oxo halide with the aluminum hydroxide and then add the selected acid to the metal mixture. The reaction may also be carried out by adding the acid to the aluminum hydroxide followed by the addition of the zirconyl hydroxy halide or zirconyl oxo halide. The reaction may also be carried out by combining the acid and the zirconyl hydroxy halide or zirconyl oxo halide followed by the addition of the aluminum hydroxide.

The amount of zirconyl hydroxy halide or zirconyl oxo halide added to the mixture is not critical as some activated AZH salt will for by the addition of any amount. It is preferred to have between 2 and 10 times the stoichiometric amount of aluminum per amount of zirconium present in the reaction mixture to produce a salt that is useful in antiperspirant compositions and meet the FDA requirements. The more preferred ratio is to have between 3 and 6 times the stoichiometric amount of aluminum present per amount of zirconium.

The activated AZH salts of this invention can be used in the preparation of antiperspirants compositions such as sticks and roll-ons using known formulations and known methods.

The method of this invention may also be used in the preparation of activated aluminum-zirconium-amino acid (AZG) salts. The activated AZG salts are produced by the co-acidification of an aluminum hydroxide and a basic zirconium carbonate followed by the addition of an amino acid such as glycine. Alternatively the activated AZG salts can be formed by the individually acidifying the aluminum hydroxide and the basic zirconium carbonate and adding an amino acid such as glycine to one of the resulting activated salt solutions and combining the two solutions.

One method for the preparation of activated AZG salts comprises the co-acidification of an aluminum hydroxide and a basic zirconium carbonate with an acid followed by the addition of an amino acid. It is preferred to use a basic zirconium carbonate paste to produce the activated AZG salts. The zirconium carbonate paste may be represented by the general formula $ZrO_2 \cdot CO_2 \cdot nH_2O$ where n is as described above. One such example of the zirconium carbonate paste is $ZrO(OH)(CO_3)_{0.5}$. The acid used in the co-acidification cf the aluminum hydroxide and zirconium carbonate paste is selected from strong acids such as HCl, HBr, HI, HF, $HNO_3$, $AlX_3$, $ZrX_4$, $ZrO(OH)X$ and $ZrOX_2$. The co-acidification takes place by combining the aluminum hydroxide and the zirconium carbonate paste followed by the addition of the strong acid. After neutralization with the acid has taken place, the amino acid is added to the solution.

The conditions for the co-acidification reaction are similar to those for the preparation of standard activated salts. It is preferred to have 2 to 10 times the stoichiometric amount of the aluminum per the amount of zirconium present in the reaction solution to produce a salt within the limits defined by the FDA. However, any amount of the aluminum hydroxide or the zirconium carbonate paste can be used and produce a salt by the method of this invention.

The amount of amino acid added into the reaction mixture is typically equivalent to the amount of zirconium added into the reaction mixture. Any amount of amino acid may be added into the reaction mixture and will result in the formation of some activated AZG, however, an amount equivalent to the amount of zirconium is one set by the industry and will produce a salt useful in antiperspirant compositions. Amino acids such as alanine, cysteine, glycine, glutamine, histidine, lysine, serine and others, are useful in the preparation of the salts. Glycine, serine and alanine are the preferred amino acid useful in the instant invention.

Another method for making the activated AZG salts comprises first producing a standard activated aluminum salt and a standard activated zirconium salt by the method of this invention, adding an amino acid to one of the salts, and combining the two activated salts to form the activated AZG salt. Any amount of standard activated aluminum and zirconium salts can be combined followed by the addition of amino acid to produce an activated AZG salt. Preferably, to meet the FDA standards, the standard activated aluminum and zirconium salts should be combined such that there is 2 to 10 time the stoichiometric amount of aluminum as there is zirconium.

It is preferable, but not essential, to add the amino acid to the standard activated zirconium salt. The amount of amino acid added should be equivalent to the amount of zirconium added as determined by industry standards. The addition of any amount of an amino acid will result in the formation of some activated AZG salt. Amino acids such as alanine, cysteine, glycine, glutamine, histidine. lysine, serine and others, are useful in the preparation of the salts. Glycine, serine and alanine are the preferred amino acid useful in the instant invention.

The activated AZG salts of this invention can be used in the preparation of antiperspirants compositions, such as sticks and roll-ons using known formulations and known methods.

The activated antiperspirant salts produced by the method of this invention are unique not only by the presence of a high concentration of peak 3 material but also by the presence of peak 1 material. When the activated salts are prepared by the method of this invention at high solids concentrations, they can be comprised of 50% or more of the $Al_{13}$ material. When the salts are prepared at low solids concentrations it is feasible to have salts that contain 70% or more of the $Al_{13}$ material. Activated antiperspirant salts produced by methods known in the art typically contain some peak 3 material and relatively none of the peak 1 material.

Even when they are prepared at low solids concentrations they can contain less than 50% of the $Al_{13}$ material.

So that those skilled in the art can understand and appreciate the invention taught herein, the following examples are presented it being understood that these examples should not be used to limit the scope of this invention over the limitations found in the claims attached hereto.

The salts were characterized using the chromatographic techniques (high pressure liquid chromatography) taught in European Patent 0,256,831.

PREP EXAMPLE 1

Preparation of Aluminum Hydroxide from $AlCl_3$

In a solution containing 80.47 grams (0.33 mole) $AlCl_3 \cdot 6H_2O$ in 240 ml of $H_2O$ an amount of 100 grams of $K_2CO_3 \cdot 1^1/_3 H_2O$ was slowly added with stirring and mild heating. When the pH of the mixture was approaching 6 a white solid $Al(OH)_3$ gel was formed that was filtered, washed many times with small amounts of distilled water and was allowed to air dry.

EXAMPLE 1

An amount of 18.75 grams (0.25 mole) of $Al(OH)_3$ prepared in Prep Example 1 was mixed with 39.5 ml of deionized water. To that mixture an amount of 10.42 ml of concentrated HCl (12M) was added dropwise under constant stirring and heating. The total addition time for the HCl was 15 minutes. During the addition of HCl, $CO_2$ was released. The solution was clear at the end of the addition of the HCl. The solution was allowed to stir for another ½ hour with the heat off. The pH of the solution was measure with pH meter to be 3.34. The salt was determined as being activated using HPLC (high performance liquid chromatography).

EXAMPLE 2

This example shows the effects of reaction temperature and reaction time on the degree of activation at varying concentrations of salt.

The typical procedure consisted of placing an amount of aluminum hydroxide wet gel, WG-100, from Chattem Chemicals in a beaker. A volume of 37 ml of 6M HCl solution was added dropwise into the solution under heat and agitation. Gas ($CO_2$) evolution occurred. After the addition of the acid was completed the mixture was allowed to stir under heat for another 15 minutes. During this time all the $Al(OH)_3$ was dissolved and a clear solution was obtained. The solid standard activated aluminum chlorohydrate formed was either precipitated out by the addition of alcohol and filtered through a Whatman #1 paper, or it was spray dried out of the solution. Spray Drying was completed by using a Nitro Atomizer with an inlet temperature of 185°–187° C. and an outlet temperature of 97°–100° C. The salt was characterized by HPLC.

The concentration, reaction temperature and reaction time were varied. Samples A, B, and C were prepared from 16.12 grams $Al(OH)_3$, 9.02 grams HCl and 24.8 grams water. Sample D was prepared from 312.5 grams $Al(OH)_3$, 220.0 grams HCl and 490.5 grams water. Sample E was prepared from 140.6 grams $Al(OH)_3$, 98.6 grams HCl and 164.0 grams water. Sample F was prepared from 351.5 grams $Al(OH)_3$, 246 grams HCl and 422.5 grams water. Samples G, H, and I were prepared from 20.16 grams $Al(OH)_3$, 11.39 grams HCl and 18.45 grams water.

Reaction conditions and results are given in Table 1. Table 2 shows the chromatographic results of the materials.

TABLE 1

| Sample | Conc. wt % | Temp. °C. | Rxn. Time hrs. | P3/P2 |
|---|---|---|---|---|
| A | 40 | 60 | 0.5 | 3.34 |
| B | 40 | 70 | 0.5 | 7.80 |
| C | 40 | 80 | 0.5 | 5.77 |
| D | 40 | 70 | 4.0 | 0.93 |
| E | 45 | 80 | 2.0 | 0.56 |
| F | 45 | 70 | 6.0 | 0.64 |
| G | 50 | 60 | 0.5 | 4.70 |
| H | 50 | 80 | 0.5 | 4.63 |
| I | 50 | 90 | 1.0 | 1.08 |

P3 = Peak 3
P2 = Peak 2

TABLE 2

| Sample | PEAK 1 A% | PEAK 2 A% | PEAK 3 A% | PEAK 4 A% | PEAK 5 A% |
|---|---|---|---|---|---|
| A | 23.09 | 10.41 | 34.80 | 22.00 | 9.71 |
| B | 24.21 | 6.36 | 49.62 | 8.17 | 11.64 |
| C | 15.72 | 9.18 | 53.60 | 8.71 | 13.39 |
| D | 30.63 | 19.61 | 18.31 | 30.40 | 1.65 |
| E | 30.80 | 35.73 | 20.02 | 11.11 | 2.34 |
| F | 33.60 | 23.43 | 14.92 | 26.33 | 1.72 |
| G | 23.32 | 11.30 | 53.16 | 12.22 | 0.00 |
| H | 17.76 | 12.09 | 55.92 | 14.23 | 0.00 |
| I | 35.26 | 23.68 | 26.52 | 8.66 | 6.88 |

A% = Area %

EXAMPLE 3

200 grams of a mixture comprised of $ZrOCl_2$ and glycine was blended with 85.9 grams $Al(OH)_3$ and 155.8 grams of water. The mixture was heated to 60° C. 58.3 grams of HCl was added at a rate of 5 ml/min. After addition of the HCl was complete, the reaction was allowed to proceed at 60° C. until the solution was clear.

The final product was filtered. HPLC analysis shows a P3/P2 ratio of 5.87. The composition of the material was Peak 1=6.05 A%, Peak 2=9.02 A%, Peak 3=52.99 A%, Peak 4=27.05 A% and Peak 5=4.29 A%.

EXAMPLE 4

Part A was prepared by adding 33.8 grams of $Al(OH)_3$ to a 70° C. solution of 21 grams of concentrated HCl in 40.1 grams of $H_2O$, with constant stirring till all was dissolved.

Part B was prepared by reacting in a round bottom flask equipped with a reflux condenser 34 grams of zirconium carbonate paste and 21 grams of concentrated HCl in 40.1 grams of $H_2O$. The solution was allowed to reflux for 1 hour. After cooling to 30° C., 8.0 grams of glycine was added.

Parts A and B were combined and characterized by HPLC. The P3/P2 ration was 2.26. The resulting product was an activated aluminum-zirconium-glycine salt. The composition of the final product was Peak 1=7.00 A%, Peak 2=10.72 A%, Peak 3=24.19 A%, Peak 4=51.37 A% and Peak 5=6.72 A%.

EXAMPLE 5

To a 70° C. solution of 105.0 grams of concentrated HCl in 227.3 grams of distilled $H_2O$ an amount of 83.3 grams of zirconium carbonate paste were mixed and 84.4 grams of Al(OH)$_3$ were added slowly until all dissolved. The solution was separated into two parts one of which was kept cold (Sample J) and the other one was placed in a round bottom flask and was allowed to reflux for 1 hour (Sample K). Four grams of glycine was added to half of each of the J and K solutions. The other half of each of the J and K solutions contained no glycine. The materials were characterized by HPLC. The P3/P2 ratios were determined to be as follows: $J^1=2.96$ $J^2=1.25$, $K^1=0.50$ and $K^2=0.65$ (1 is no glycine and 2 is glycine). The compositions of the solutions are in Table 3. The solutions that did not contain glycine gelled within 24 hours.

TABLE 3

| Sample | PEAK 1 A% | PEAK 2 A% | PEAK 3 A% | PEAK 4 A% | PEAK 5 A% |
|---|---|---|---|---|---|
| J1 | 33.45 | 3.24 | 9.58 | 45.37 | 8.35 |
| J2 | 20.89 | 7.05 | 8.84 | 62.61 | 0.00 |
| K1 | 28.94 | 17.49 | 8.67 | 34.04 | 10.85 |
| K2 | 19.06 | 20.05 | 13.05 | 38.82 | 8.42 |

COMPARATIVE EXAMPLE 1

A sample was prepared according to the method as taught in Canadian Patent No. 1,118,357 (equivalent to U.S. Pat. No. 4,359,456).

Approximately 30 gallons of a 20% by weight aluminum chlorohydrate in water solution was loaded into a 50 gallon reactor equipped with an agitator and a steam jacket. The contents of the reactor were heated to approx. 120° over a period of 1 hour and 15 minutes and held at 120° for 4 hours. The salt was spray dried at an inlet, outlet and feed temperature of 245°–250° C., 92°–94° C. and 136° F. respectively. HPLC analysis show a material comprised of 55.4 Area % "Peak 2" and 44.6 area % "Peak 3". There was no "Peak 1" material formed.

What is claimed is:

1. A method for preparing activated aluminum-zirconium-amino acid salts comprising:
   (I) reacting
      (A) zirconium carbonate and
      (B) aluminum hydroxide; with
      (C) an acid selected from HCl, HI, HBr, HF, HNO$_3$, AlX$_3$, ZrX$_4$, ZrO(OH)X, and ZrOX$_2$, wherein X is selected from Cl, Br and I and wherein there is between 2 and 10 times the stoichiometric amount of aluminum per amount of zirconium present in the reaction mixture; and
   (II) adding an amino acid to the reaction product of (I); and
   (III) recovering the reaction product of (II).

2. A method as claimed in claim 1, wherein the amino acid is glycine.

3. A method for preparing activated aluminum-zirconium-amino acid salts, comprising:
   (I) producing an activated aluminum salt by
      (i) reacting at a temperature of less than 100° C.
         (A) aluminum hydroxide and
         (B) HCl
      (ii) reacting at a temperature of less than 100° C.
         (A) zirconium carbonate with
         (B) HCl
      (iii) adding an amino acid to the activated zirconium salt produced in (ii);
      (iv) combining the activated aluminum salt (i) and the activated zirconium/amino acid salt (iii) to react same wherein there is between 2 and 10 times the stoichiometric amount of aluminum per amount of zirconium present in the reaction mixture; and
      (v) recovering from solution the activated aluminum-zirconium salt of (iv).

4. A method as claimed in claim 3 wherein the amino acid is glycine.

5. A method for preparing activated aluminum-zirconium-amino acid salts, comprising:
   (I) producing an activated aluminum salt by
      (i) reacting at a temperature of less than 100° C.
         (A) zirconium hydroxide and
         (B) HCl
      (ii) reacting at a temperature of less than 100° C.
         (A) zirconium carbonate with
         (B) HCl
      (iii) adding an amino acid to the activated aluminum salt produced in (i);
      (iv) combining the activated aluminum/amino acid salt (iii) and the activated zirconium acid salt (ii) to react same wherein there is between 2 and 10 times the stoichiometric amount of aluminum per amount of zirconium present in the reaction mixture; and
      (v) recovering from solution the activated aluminum-zirconium salt of (iv).

6. A method as claimed in claim 5, wherein the amino acid is glycine.

* * * * *